(12) United States Patent
Torres Morales

(10) Patent No.: US 10,456,587 B2
(45) Date of Patent: Oct. 29, 2019

(54) TERMINAL CONNECTOR INSERTION TOOL AID

(71) Applicant: Cardiac Pacemakers, Inc., St. Paul, MN (US)

(72) Inventor: Luis Antolin Torres Morales, Dorado, PR (US)

(73) Assignee: Cardiac Pacemakers, Inc., St. Paul, MN (US)

(*) Notice: Subject to any disclaimer, the term of this patent is extended or adjusted under 35 U.S.C. 154(b) by 198 days.

(21) Appl. No.: 15/182,395

(22) Filed: Jun. 14, 2016

(65) Prior Publication Data

US 2016/0367820 A1 Dec. 22, 2016

Related U.S. Application Data

(60) Provisional application No. 62/181,751, filed on Jun. 18, 2015.

(51) Int. Cl.
*A61N 1/00* (2006.01)
*A61N 1/375* (2006.01)
*A61N 1/05* (2006.01)

(52) U.S. Cl.
CPC .............. *A61N 1/3752* (2013.01); *A61N 1/05* (2013.01)

(58) Field of Classification Search
CPC ........ A61N 1/05; A61N 1/056; A61N 1/3752; A61N 2001/0578
See application file for complete search history.

(56) References Cited

U.S. PATENT DOCUMENTS

| | | | |
|---|---|---|---|
| 4,512,351 A | 4/1985 | Pohndorf | |
| 6,445,954 B1 * | 9/2002 | Olive | A61N 1/056 607/37 |
| 7,993,305 B2 * | 8/2011 | Ye | A61M 25/0668 604/164.05 |
| 8,666,514 B2 | 3/2014 | Tockman et al. | |
| 2010/0137929 A1 * | 6/2010 | Libbey | A61N 1/3752 607/5 |
| 2015/0080851 A1 * | 3/2015 | Kurth | A61M 25/0097 604/507 |

FOREIGN PATENT DOCUMENTS

EP 1663390 B1 1/2011

* cited by examiner

*Primary Examiner* — Mallika D Fairchild
(74) *Attorney, Agent, or Firm* — Faegre Baker Daniels, LLP

(57) ABSTRACT

Aspects of the present disclosure are directed toward methods, systems, and apparatuses that include an insertion tool configured to removeably secure to an implantable lead. The implantable lead may be connected to an implantable medical device by applying longitudinal force to the insertion tool. The insertion tool may subsequently be removed.

15 Claims, 4 Drawing Sheets

TERMINAL CONNECTOR INSERTION TOOL AID

CROSS-REFERENCE TO RELATED APPLICATION

This application claims priority to Provisional Application No. 62/181,751, filed Jun. 18, 2015, which is herein incorporated by reference in its entirety.

TECHNICAL FIELD

The present disclosure relates to medical devices including one or more leads. More specifically, the disclosure relates to devices and methods for facilitating connection between a lead and a medical device.

BACKGROUND

Medical systems that are used for diagnostic purposes such as for stimulating a target nerve or patient's heart often include a lead assembly and a medical device with the lead assembly. The lead assembly may comply with one or more of the IS1, IS4, DF4 standards, or a custom terminal connector design. Further, a header of the medical device (such as an implantable pulse generator) generally includes corresponding connector ports that provide connections to the lead assembly. A proper connection between the leads and the corresponding connector ports is required to allow proper functioning of the system.

SUMMARY

In Example 1, a method of connecting a lead to a medical device, the lead including a flexible body having a distal end, and a proximal end having a connector configured to plug into a connection port of the medical device, the method comprising: removeably securing the proximal end of the lead within a lumen of an insertion tool; grasping an exterior portion of the insertion tool; applying longitudinal force, along the length of the lead, to the insertion tool while grasping the exterior portion of the insertion tool; inserting the connector into a connection port of the medical device, wherein applying longitudinal force to the insertion tool overcomes a resistance between the connector and the connection port; and removing the insertion tool from the lead after the connector is plugged into the connection port of the medical device.

In Example 2, the method of Example 1, wherein removeably securing the proximal end of the lead within the lumen of the insertion tool comprises sliding the insertion tool from the proximal end until the insertion tool frictionally engages the lead.

In Example 3, the method of Example 1 or 2, wherein removeably securing the proximal end of the lead within the lumen of the insertion tool comprises arranging the insertion tool, having a cylindrical body, near the proximal end of the lead.

In Example 4, the method of Example 3, wherein the cylindrical body comprises at least two different materials.

In Example 5, the method of Example 4, wherein the at least two different materials include a first material and a second material, the first material having a greater axial strength than the second material.

In Example 6, the method of any of Examples 1-5, wherein removing the insertion tool from the lead comprises peeling the insertion tool.

In Example 7, the method of Example 6, wherein removing the insertion tool comprises applying a force to split the insertion tool.

In Example 8, the method of any of Examples 1-7, wherein removeably securing the proximal end of the lead within the lumen of the insertion tool comprises arranging the insertion tool having a cylindrical body comprising opposing radial projections.

In Example 9, the method of Example 8, wherein removing the insertion tool comprises applying longitudinal force to the opposing radial projections to split the cylindrical body of the insertion tool.

In Example 10, the method of Example 9, wherein applying the longitudinal force to the opposing radial projections in a direction opposite that of the medical device.

In Example 11, an apparatus comprising: a medical device including at least one connection port; a lead including a flexible body having a distal end, and a proximal end having a connector configured to plug into a connection port of the medical device; and an insertion tool configured to removeably secure near the proximal end of the lead, the insertion tool further configured to: translate a first force applied longitudinally along the length of the lead for inserting the connector into a connection port of the medical device, the first applied longitudinal force being in a direction toward the medical device, and release from the lead in response to application of a second force.

In Example 12, the apparatus of Example 11, wherein the insertion tool comprises a cylindrical body.

In Example 13, the apparatus of Example 12, wherein the insertion tool further comprises opposing radial projections arranged on the cylindrical body.

In Example 14, the apparatus of Example 13, wherein the radial projections comprise a first material and the cylindrical body comprises a second material.

In Example 15, the apparatus of Example 14, wherein the first material is of a greater axial strength than the second material, and the second material is configured to split in response to the second force.

In Example 16, a method of connecting an implantable lead to an implantable medical device, the implantable lead including a flexible body having a distal end, and a proximal end having a connector configured to plug into a connection port of the implantable medical device, the method comprising: removeably securing the proximal end of the implantable lead within a lumen of an insertion tool; grasping an exterior portion of the insertion tool; applying longitudinal force, along the length of the implantable lead, to the insertion tool while grasping the exterior portion of the insertion tool; inserting the connector into a connection port of the implantable medical device, wherein applying longitudinal force to the insertion tool overcomes a resistance between the connector and the connection port; and removing the insertion tool from the implantable lead after the connector is plugged into the connection port of the implantable medical device.

In Example 17, the method of Example 16, wherein removeably securing the proximal end of the implantable lead within the lumen of the insertion tool comprises arranging the insertion tool having a cylindrical body near the proximal end of the implantable lead.

In Example 18, the method of Example 16, further comprising providing an additional implantable lead, and removeably securing an additional insertion tool on the additional implantable lead, grasping an exterior portion of the additional insertion tool, applying longitudinal force, along the length of the implantable lead, to the additional insertion tool while grasping the exterior portion of the additional insertion tool, and connecting the additional implantable lead to an additional connection port of the implantable medical device.

In Example 19, the method of Example 18, wherein the additional insertion tool is sized to permit connecting the additional implantable lead to the connection port of the implantable medical device after inserting the connector of the implantable lead into the connection port of the implantable medical device, and further comprising removing the additional insertion tool from the additional implantable lead after connecting the additional implantable lead to the additional connection port of the implantable medical device.

In Example 20, the method of Example 19, wherein removing the insertion tool from the implantable lead comprises at least one of peeling the insertion tool, and applying a force to split the insertion tool.

In Example 21, the method of Example 16, wherein removeably securing the insertion tool comprises providing a cylindrical body having opposing radial projections.

In Example 22, the method of Example 21, wherein removing the insertion tool comprises applying longitudinal force to the opposing radial projections to split the cylindrical body of the insertion tool.

In Example 23, the method of Example 22, wherein removing the insertion tool comprises applying the longitudinal force to the opposing radial projections in a direction opposite that of the implantable medical device.

In Example 24, the method of Example 16, wherein removeably securing the proximal end of the implantable lead within the lumen of the insertion tool comprises applying longitudinal force insertion tool a direction opposite that of the implantable medical device.

In Example 25, the method of Example 16, wherein removeably securing the proximal end of the implantable lead within the lumen of the insertion tool providing the insertion tool comprising a first material and a second material.

In Example 26, the method of Example 25, wherein the first material having a greater axial strength or tear strength than the second material.

In Example 27, the method of Example 26, wherein removeably securing the proximal end of the implantable lead within the lumen of the insertion tool providing the insertion tool comprises a first material and a second material.

In Example 28, a method of connecting an implantable lead to an implantable medical device, the implantable lead including a flexible body having a distal end, and a proximal end having a connector configured to plug into a connection port of the implantable medical device, the method comprising: removeably securing an insertion tool near the proximal end of the implantable lead, the insertion tool comprising a cylindrical body configured to divide upon application of a splitting force; applying axial force to the insertion tool; applying longitudinal force, along the length of the implantable lead, to the insertion tool while applying axial force to the insertion tool; inserting the connector into a connection port of the implantable medical device, wherein applying longitudinal force to the insertion tool overcomes a resistance between the connector and the connection port; and removing the insertion tool after inserting the connector into a connection port of the implantable medical device by applying the splitting force to the cylindrical body of the insertion tool.

In Example 29, the method of Example 28, wherein removeably securing the proximal end of the implantable lead within the lumen of the insertion tool comprises sliding the insertion tool from the proximal end until the lumen of the insertion tool frictionally engages the implantable lead.

In Example 30, the method of Example 28, wherein applying the longitudinal force, along the length of the implantable lead, to the insertion tool comprises frictionally engaging the insertion tool with the implantable lead.

In Example 31, the method of Example 28, wherein removing the insertion tool comprises applying the splitting force in a direction opposite the implantable medical device.

In Example 32, an apparatus comprising an implantable medical device including at least one connection port; an implantable lead including a flexible body having a distal end, and a proximal end having a connector; and an insertion tool removeably secured near the proximal end of the implantable lead, the insertion tool comprising a first material and a second material, wherein the first material has a greater axial strength or tear strength than the second material.

In Example 33, the apparatus of Example 32, wherein the insertion tool comprises a cylindrical body and opposing radial projections, and wherein the opposing radial projections comprise a first material, and the cylindrical body comprise a second material.

In Example 34, the apparatus of Example 32, further comprising an engagement area arranged on the implantable lead, and wherein the insertion tool is sized to fit over the engagement area.

In Example 35, the apparatus of Example 34, further comprising an engagement area arranged on the implantable lead having at least a portion that includes silicone, and wherein the second material is silicone, and the window or gaps allows viewing of the engagement area.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
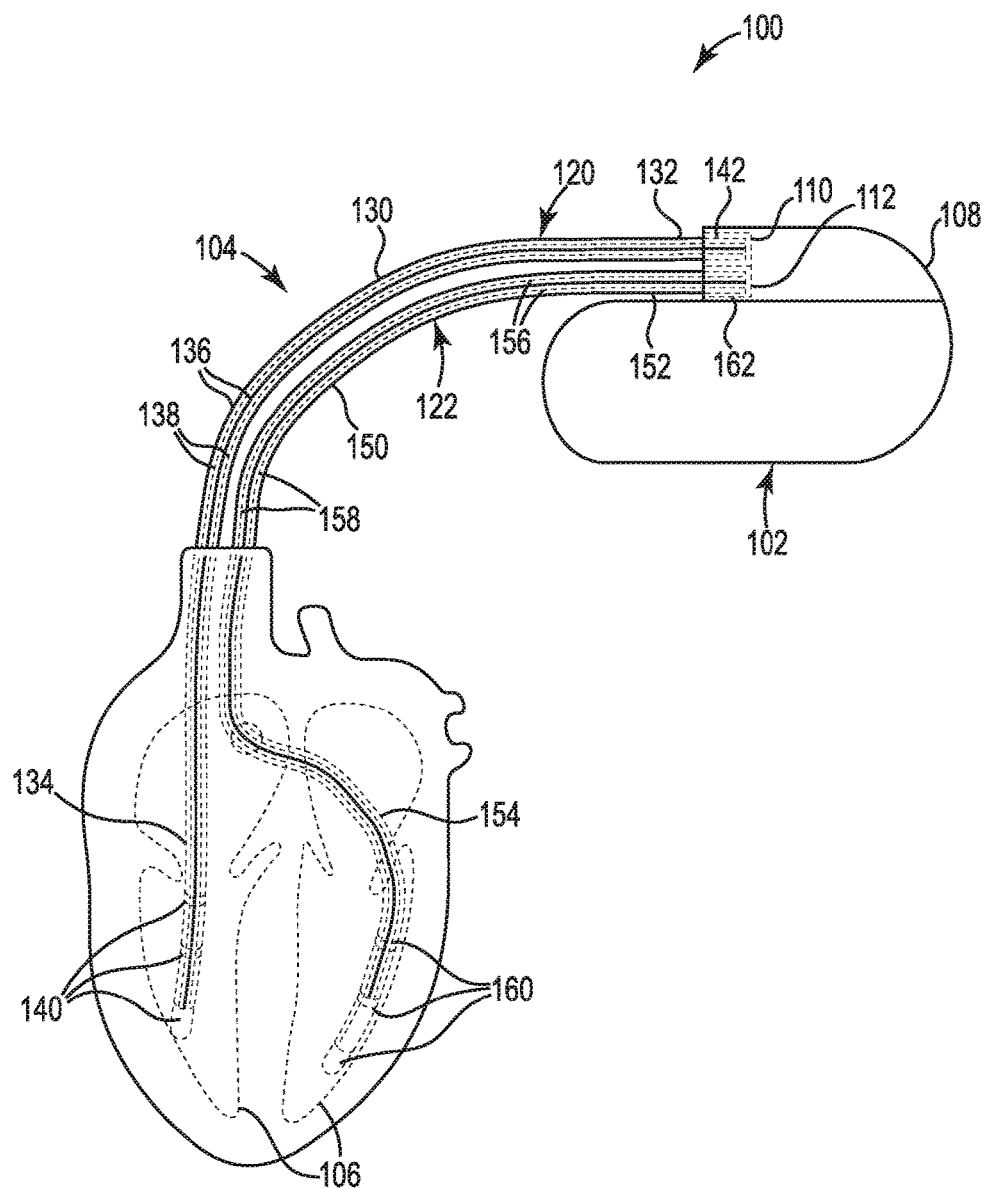
FIG. 1 shows a schematic illustration of an exemplary implantable system having an implantable medical device and an implantable lead assembly.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

FIG. 1 shows a schematic illustration of an exemplary implantable system 100 having an implantable medical device 102 and an implantable lead assembly 104. As shown, the implantable medical device 102 is connected to the implantable lead assembly 104. In various embodiments, the implantable medical device 102 is an implantable pulse generator adapted to generate electrical signals to be delivered to a target location 106. In various embodiments, the implantable medical device 102 is a pulse generator such as a pacemaker, an implantable cardioverter/defibrillator (ICD), a cardiac resynchronization (CRT) device, and/or a neurostimulator, and may be configured to deliver one or more of pacing, CRT, defibrillation, and neurostimulation therapies. As shown, the target location 106 is in a patient's heart, however other implant locations are possible. The implantable medical device 102 may be configured to generate electrical signals to pace and/or sense electrical activity at a location on or within the heart, or to stimulate and/or sense electrical activity at a location on or within the brain and/or nervous system.

The implantable medical device 102 may include a header 108. As shown in FIG. 1, the header 108 includes a first connector port 110 and a second connector port 112, however, the header 108 may also include a single connection port, or more than two connection ports. In addition, the implantable lead assembly 104 is shown as including a first implantable lead 120 connected to the first connector port 110 and a second implantable lead 122 connected to the second connector port 112. The implantable lead assembly 104 may include a single implantable lead, or more than two implantable leads.

Each of the first and second implantable leads 120, 122 may include a flexible lead body, one or more conductor wires, one or more electrodes, and a terminal connector assembly. For example, as shown, the first implantable lead 120 may include a flexible lead body 130 having a proximal end 132, a distal end portion 134, and one or more conductor lumens 136 extending axially within the lead body 130 from the proximal end 132 to the distal end portion 134. The first implantable lead 120 may also include one or more wires 138, each conductor wire extending within one of the conductor lumens 136 in the lead body 130. The first implantable lead 120 may further include one or more electrodes 140 coupled to the distal end portion 134 of the lead body 130. The one or more electrodes 140 are electrically coupled to at least one of one or more of the conductor wires 138. The first implantable lead 120 may also include a terminal connector 142 coupled to the proximal end 132 of the lead body 130. The terminal connector 142 is sized to be inserted into and received by the first connector port 110 of the header 108.

Similarly, the second implantable lead 122 may include a flexible lead body 150 having a proximal end 152, a distal end portion 154, and one or more lumens 156 extending axially within the lead body 150 from the proximal end 152 to the distal end portion 154. The second implantable lead 122 may also include one or more wires 158, each conductor wire extending within one of the conductor lumens 156 in the lead body 150. Further, the second implantable lead 122 may include one or more electrodes 160 coupled to the distal end portion 154 of the lead body 150. The one or more electrodes 160 are electrically coupled to at least one of the one or more conductor wires 158. The second implantable lead 122 may also include a terminal connector assembly 162 coupled to the proximal end 152 of the lead body 150. The terminal connector assembly 162 is sized to be inserted into and received by the second connector port 112 of the header 108.

Connecting one or more of the implantable leads 120, 122 to the header 108 may be difficult due to the fit between the terminal connectors 142, 162 and the connector ports 110, 112. To overcome frictional forces and properly fit the terminal connector 142, 162 within the connector ports 110, 112, an operating physician or trained person may apply a longitudinal force, along the length of the implantable leads 120, 122, and toward the header 108. In applying this force, however, the person handling the implantable leads 120, 122 may apply a radial force to the flexible lead bodies, and potentially damage the internal components (e.g., conductor wire(s)) of the implantable leads 120, 122. Damaging the internal components of the implantable leads 120, 122 may hinder the performance of the implantable leads 120, 122, or render the implantable leads 120, 122 functionless.

The first implantable lead 120 and/or the second implantable lead 122 may be configured to comply with the IS4 standard (low voltage) and the first implantable lead 120 and/or the second implantable lead 122 may be configured to comply with the DF4 standard (high voltage). Similarly, the first connector port 110 and/or the second connector port 112 may be configured to comply with the IS4 standard and the first connector port 110 and/or the second connector port 112 may be configured to comply with the DF4 standard. In some embodiments, the implantable lead assembly 104 may also include a third implantable lead (not shown) and the header 108 may include a corresponding third connector port (not shown). In certain embodiments, the third implantable lead and the third connector port may be configured to comply with the IS1 (low voltage) standard. The first connector port 110 and/or the second connector port 112 may be custom made terminals.

Figure 2A:
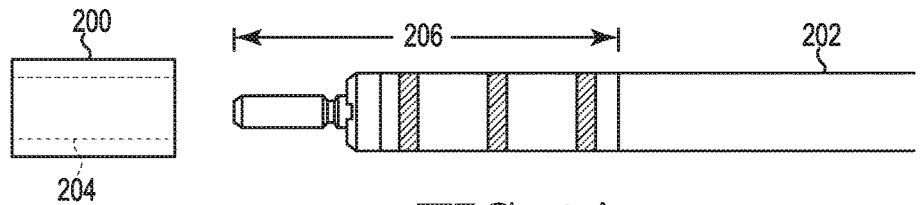
FIG. 2A shows a schematic illustration of an exemplary insertion tool and implantable lead.

FIG. 2A shows a schematic illustration of an exemplary insertion tool 200 and implantable lead 202. As shown, the insertion tool 200 may have a cylindrical body. The cylindrical body may be of a different shape such as a ring, a box, or another three-dimensional structure. The insertion tool 200 may also include an inner lumen 204. The inner lumen 204 of the insertion tool 200 is sized to translate over a portion of an exterior surface of the implantable lead 202. The insertion tool 200 may be provided at either end of the implantable lead 202. As shown, a proximal end of the implantable lead 202 is shown including a connector assembly 206. The insertion tool 200 may be positioned on the implantable lead 202 by arranging and removeably securing a portion via the proximal end, and over the connector assembly 206 of the implantable lead 202. The implantable lead 202 is provided within the lumen 204 of the insertion tool 200.

Figure 2B:
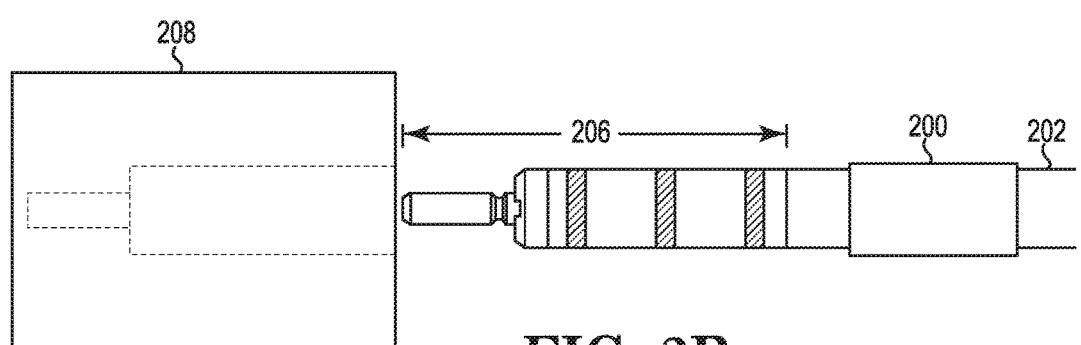
FIG. 2B shows a schematic illustration of the exemplary insertion tool removeably secured to the implantable lead shown in FIG. 2A.

FIG. 2B shows a schematic illustration of the exemplary insertion tool 200 removeably secured to the implantable lead 202 shown in FIG. 2A. After the insertion tool 200 is removeably secured to the implantable lead 202, a user, such as an operating physician or trained person, may maneuver the implantable lead 202 by grasping an exterior surface of the insertion tool 200. Grasping an exterior surface of the insertion tool 200 avoids damaging the internal components of the implantable lead 202 as noted above with reference to FIG. 1. The user may directly grasp the exterior surface of the insertion tool 200, for example, by gripping the insertion tool 200 between the user's fingers. The user may also indirectly grasp the exterior surface of the insertion tool 200, for example, by gripping the insertion tool 200 with a forceps, tongs, or any other acceptable grasping mechanism. The user may then insert the implantable lead 202 into a header 208.

Figure 2C:
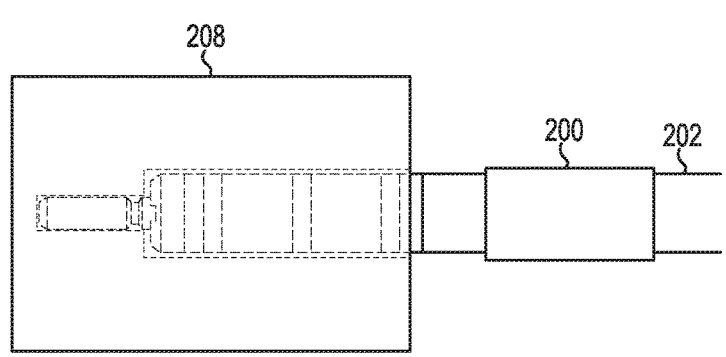
FIG. 2C shows a schematic illustration of the exemplary insertion tool removeably secured to the implantable lead as shown in FIG. 2B and connected to a connector port.

FIG. 2C shows a schematic illustration of the exemplary insertion tool 200 removeably secured to the implantable lead 202 as shown in FIG. 2B and connected to the header 208 via a connector port (shown in phantom). As shown in FIG. 2C, the user may maneuver the implantable lead 202 into the header 208 by gripping the insertion tool 200. The insertion tool 200 may provide a protective surface for the implantable lead 202 such that the insertion tool 200 absorbs the radial force of a user's gripping of the insertion tool 200. In addition, connecting the implantable lead 202 to the header 208 may include applying longitudinal force to the implantable lead 202 via the insertion tool 200 such that the applying the longitudinal force to the insertion tool 200 overcomes a resistance between the connector assembly 206 and the header 208. The connector assembly 206 is shown phantom as connected to the header 208.

Figure 2D:
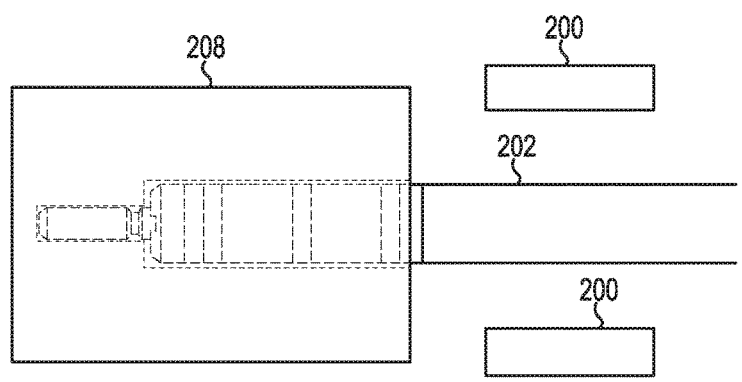
FIG. 2D shows a schematic illustration of the exemplary insertion tool removed from the implantable lead connected to the connector port as shown in FIG. 2C.

FIG. 2D shows a schematic illustration of the exemplary insertion tool 200 removed from the implantable lead 202 connected to the header 208 as shown in FIG. 2C. After the implantable lead 202 is connected to the header 208, the insertion tool 200 may be removed/released from the implantable lead 202. The insertion tool 200 may be removed/released from the implantable lead 202 by applying a force to the exterior body of the insertion tool 200. The force may be a peeling force applied to one or more portions of the insertion tool 200. The peeling force may be applied by grasping one or more edges of the exterior portion of the insertion tool 200, and applying a radially outward force until the insertion tool 200 divides into two or more portions, such as shown in FIG. 2D. The force may also be a splitting force applied to one or more portions of the insertion tool 200. The splitting force may be applied by applying sheer forces to the exterior portion of the insertion tool 200 or one or more edges of the exterior portion of the insertion tool 200 until the insertion tool 200 divides into two or more portions, such as shown in FIG. 2D.

Figure 3A:
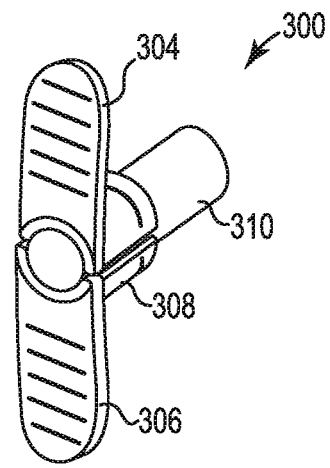
FIG. 3A shows a perspective view of a schematic illustration of another exemplary insertion tool.

FIG. 3A shows a perspective view of a schematic illustration of another exemplary insertion tool 300. The insertion tool 300 is shown including first and second projections 304, 306 and a cylindrical body. Although the insertion tool 300 is shown with first and second projections 304, 306, it will be understood that the insertion tool 300 may also include a single radial projection, or plurality of radial projections. The first and second projections 304, 306 are shown disposed about a cylindrical body that may include a first portion 308 and a second portion 310. The first portion 308 and may comprise a first material, and the second portion 310 (cylindrical body section) may comprise a second material. In addition, the first and second projections 304, 306, shown attached to the first portion 308, may also be formed of the first material. In certain instances, the first material is of a greater axial strength (and/or tear strength) than the second material.

Figure 3B:
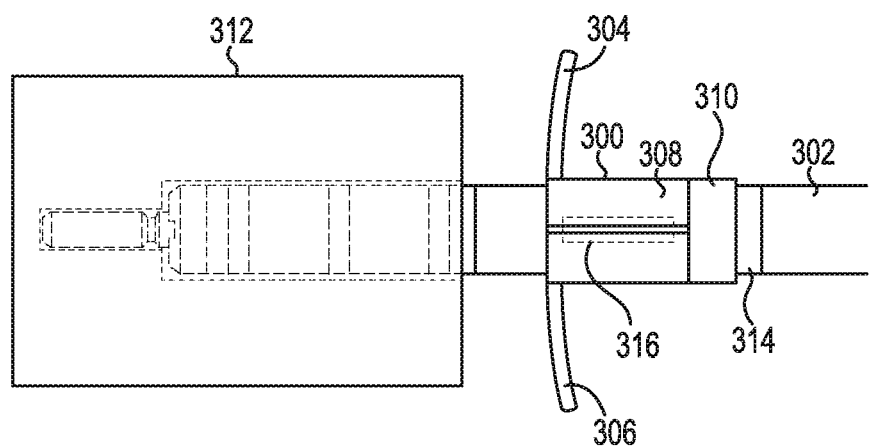
FIG. 3B shows a schematic illustration of the exemplary insertion tool shown in FIG. 3A as removeably secured to an implantable lead.

FIG. 3B shows a schematic illustration of the exemplary insertion tool shown in FIG. 3A as removeably secured to an implantable lead 302. As shown in FIG. 3B, the insertion tool 300 is removeably secured to the implantable lead 302, and the implantable lead 302 is connected to a header 312. A connector assembly (as described above) of the implantable lead 302 is shown in phantom as connected to a connector port (shown in phantom) of the header 312.

The insertion tool 300 is configured to translate a first force applied longitudinally along the length of the implantable lead 302 for inserting a connector portion of the implantable lead 302 into the header 312 (of an implantable medical device). The first longitudinal force is applied in a direction toward the header 312. In addition, the insertion tool 300 may be configured to release from the implantable lead 302 in response to application of a second force (as is discussed in further detail below with reference to FIG. 4). The second force may be a peeling force applied to one or more portions of the insertion tool 300. The peeling force may be applied by grasping the first and second projections 304, 306 of the insertion tool 300, and applying a radially outward force to the first and second projections 304, 306 until the insertion tool 300 divides to allow for the insertion tool 300 to be removed from the implantable lead 302. The insertion tool 300 may divide into two or more portions, or may also split along one axis to allow for the insertion tool 300 to slip off the implantable lead 302. The force may also be a splitting force applied to the first and second projections 304, 306 of the insertion tool 300. The splitting force applied to the first and second projections 304, 306 provides sheer forces to the insertion tool 300 until the insertion tool 300 divides into two or more portions. In certain instances, applying the force to remove the insertion tool 300 from the implantable lead 302 may split or divide the second portion 310 of the insertion tool 300. The first portion 308 and the second portion 310 of the insertion tool 300 may be provided as separate sections such that, other than the attachment between the two portions, the first portion 308 the second portion 310 do not overlap. The first portion 308 and the second portion 310 of the insertion tool 300 may be provided as overlapping sections. For example, the second portion 310 may be provided as an interior layer to the first portion 308. In such an embodiment, the second portion 310 may extend beyond either side of the first portion 308, as is shown in FIG. 3. The second portion 310, and the second material, may be configured to frictionally engage a portion of the implantable lead 302 to removeably secure the insertion tool 300 to the implantable lead 302. In addition, the second portion 310, and the second material, is also configured to split in response to the second force. The second material may comprise silicone, or a similar such flexible material that provides tack or grip longitudinally along a body, such as an implantable lead, that may be enhanced by way of an inward force. The first material may comprise a rigid or semi-rigid plastic.

The portion of the implantable lead 302, referred to as an engagement area 314, may be characterized as the portion at which the insertion tool 300 frictionally engages the implantable lead 302 to removeably secure the insertion tool 300 to the implantable lead 302. The engagement area 314 is separated from the connector assembly portion (not shown) of the implantable lead 302. The engagement area 314 may have a surface that is not distinguishable from the remaining portions of the implantable lead 302. In certain instances, the engagement area 314 may be included of an additional material (e.g., silicone) formed on the exterior surface of the implantable lead 302.

The insertion tool 300 may also include a window/gap 316. The window/gap 316 may be transparent, or may be provided by creating a gap in material. The window/gap 316 may be provided in the first portion 308 of the insertion tool 300. Additional material provided as a portion of the engagement area 314 may include information (e.g., serial number) that describes the unique aspects of the implantable lead 302. The window/gap 316 allows for an operating physician, or other user, to view the information while using the insertion tool 300.

Figure 4:
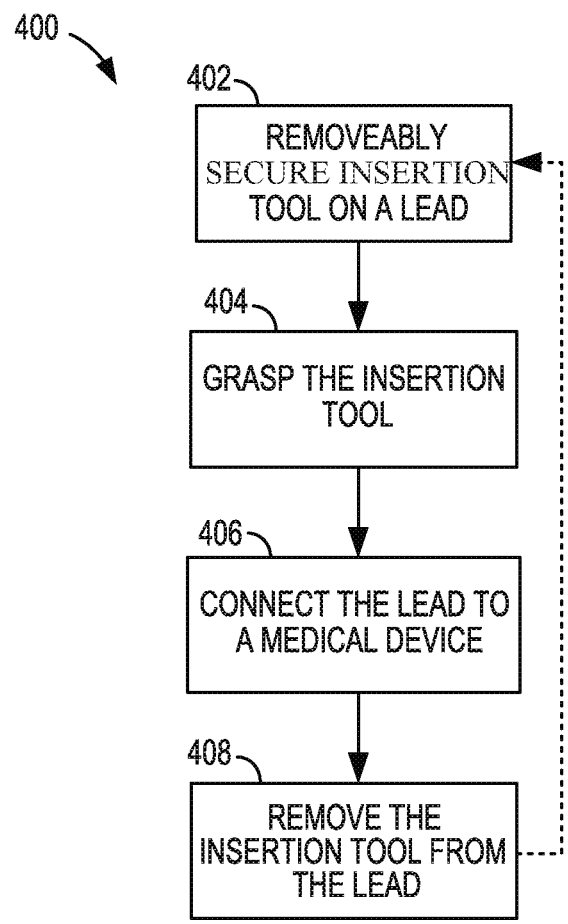
FIG. 4 is a flow chart depicting an exemplary method of connecting an implantable lead to an implantable medical device.

FIG. 4 is a flow chart 400 depicting an exemplary method of connecting an implantable lead to an implantable medical device. As is shown at block 402, the method includes removeably securing an implantable lead within a lumen of an insertion tool. The implantable lead may include a flexible body having a distal end, and a proximal end having a connector configured to plug into a connection port of the implantable medical device. Removeably securing the insertion tool to the implantable lead may include sliding the insertion tool from the proximal end until the lumen of the insertion tool frictionally engages the implantable lead.

In certain instances, the proximal end of the implantable lead, or a portion thereof, is secured within a lumen of the insertion tool. The method may include sliding the insertion tool from the proximal end until the insertion tool frictionally engages the implantable lead. As discussed above with reference to FIGS. 2A-2D and FIG. 3, the insertion tool may have a cylindrical body. In addition, the cylindrical body may comprise at least two different materials. In certain instances, two different materials may include a first material and a second material with the first material having a greater axial strength (and/or tear strength) than the second material. The insertion tool may also include radial projections disposed about the cylindrical body.

As is shown at block 404, the method includes grasping an exterior portion of the insertion tool. Grasping the insertion tool avoids damaging the internal components of the implantable lead. A user may directly grasp the exterior surface of the insertion tool, for example, by gripping the insertion tool between the user's fingers. The user may also indirectly grasp the exterior surface of the insertion tool, for example, by gripping the insertion tool with a forceps, tongs, or any other acceptable grasping mechanism.

As is shown at block 406, the method also includes connecting the lead to a medical device. In certain instances, this step includes applying longitudinal force, along the length of the implantable lead, to the insertion tool while grasping the exterior portion of the insertion tool. Further, the method may also include inserting the connector into a connection port of the implantable medical device. Applying longitudinal force to the insertion tool overcomes a resistance between the connector and the connection port. Applying longitudinal force may include frictionally engaging the insertion tool with the implantable lead.

As is shown at block 408, the method also includes removing the insertion tool from the implantable lead after the connector is plugged into the connection port of the implantable medical device. Removing the insertion tool from the implantable lead may include peeling the insertion tool off of the implantable lead. In addition, removing the insertion tool may include applying a force to split the insertion tool. In instances where the insertion tool includes radial projections, removing the insertion tool may include applying longitudinal force to the opposing radial projections to split the cylindrical body of the insertion tool. The longitudinal force to the opposing radial projections in a direction opposite that of the implantable medical device.

In certain instances, each of the steps discussed with reference to FIG. 4 may be repeated for connecting one or more additional implantable leads to the medical device. As shown in FIG. 1, for example, a medical device may include one or more connection ports. Thus, the method may also include providing an additional implantable lead, and arranging an additional insertion tool on the additional implantable lead, grasping an exterior portion of the additional insertion tool, applying longitudinal force, along the length of the implantable lead, to the additional insertion tool while grasping the exterior portion of the additional insertion tool, and connecting the additional implantable lead to an additional connection port of the implantable medical device. In addition, the method may include removing the additional insertion tool from the additional implantable lead after connecting the additional implantable lead to the additional connection port of the implantable medical device. The insertion tools, described herein, may be sized to permit connecting the additional implantable lead to the connection port of the implantable medical device after inserting the connector of the implantable lead into the connection port of the implantable medical device.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

I claim:

1. A method of connecting an implantable lead to an implantable medical device, the implantable lead including a flexible body having a distal end, and a proximal end having a connector configured to plug into a connection port of the implantable medical device, the method comprising:
    removeably securing the proximal end of the implantable lead within a lumen of an insertion tool including a proximal end and a distal end and having a first portion comprising a first material including radial projections and a second portion comprising a second material configured to frictionally engage the implantable lead, the first portion at least partially arranged circumferentially about the second portion at or adjacent to the distal end of the insertion tool;
    grasping an exterior portion of the insertion tool;
    applying longitudinal force, along the length of the implantable lead, to the insertion tool while grasping the exterior portion of the insertion tool;
    inserting the connector into a connection port of the implantable medical device, wherein applying longitudinal force to the insertion tool overcomes a resistance between the connector and the connection port; and
    removing the insertion tool from the implantable lead after the connector is plugged into the connection port of the implantable medical device by splitting the insertion tool into two or more pieces along the second material.

2. The method of claim 1, wherein removeably securing the proximal end of the implantable lead within the lumen of the insertion tool comprises arranging the insertion tool having a cylindrical body near the proximal end of the implantable lead.

3. The method of claim 1, further comprising providing an additional implantable lead, and removeably securing an additional insertion tool on the additional implantable lead, grasping an exterior portion of the additional insertion tool, applying longitudinal force, along the length of the implantable lead, to the additional insertion tool while grasping the exterior portion of the additional insertion tool, and connecting the additional implantable lead to an additional connection port of the implantable medical device.

4. The method of claim 3, wherein the additional insertion tool is sized to permit connecting the additional implantable lead to the connection port of the implantable medical device after inserting the connector of the implantable lead into the connection port of the implantable medical device, and further comprising removing the additional insertion tool from the additional implantable lead after connecting the additional implantable lead to the additional connection port of the implantable medical device.

5. The method of claim 1, wherein removing the insertion tool from the implantable lead comprises at least one of peeling the insertion tool, and applying a force to split the insertion tool.

6. The method of claim 1, wherein removeably securing the insertion tool comprises providing a body portion that is a cylindrical.

7. The method of claim 6, wherein removing the insertion tool comprises applying longitudinal force to the opposing radial projections to split the cylindrical body of the insertion tool.

8. The method of claim 7, wherein removing the insertion tool comprises applying the longitudinal force to the opposing radial projections in a direction opposite that of the implantable medical device.

9. The method of claim 1, wherein removeably securing the proximal end of the implantable lead within the lumen of the insertion tool comprises applying a longitudinal force to the insertion tool a direction opposite that of the implantable medical device.

10. The method of claim 1, wherein the first material having a greater axial strength or tear strength than the second material.

11. The method of claim 10, wherein removing the insertion tool from the implantable lead after the connector is plugged into the connection port of the implantable medical device comprises splitting the insertion tool along the second material.

12. A method of connecting an implantable lead to an implantable medical device, the implantable lead including a flexible body having a distal end, and a proximal end having a connector configured to plug into a connection port of the implantable medical device, the method comprising:

removeably securing an insertion tool near the proximal end of the implantable lead, the insertion tool including a proximal end and a distal end and comprising a cylindrical body configured to divide upon application of splitting force having a first portion comprising a first material and a second portion comprising a second material configured to frictionally engage the implantable lead and with the first material having a greater axial strength or tear strength than the second material, the first portion at least partially arranged circumferentially about the second portion at or adjacent to the distal end of the insertion tool;

applying axial force to the insertion tool;

applying longitudinal force, along the length of the implantable lead, to the insertion tool while applying axial force to the insertion tool;

inserting the connector into a connection port of the implantable medical device, wherein applying longitudinal force to the insertion tool overcomes a resistance between the connector and the connection port; and removing the insertion tool after inserting the connector into a connection port of the implantable medical device by applying the splitting force to the cylindrical body of the insertion tool to create a tear in the second material and separate the insertion tool into two or more pieces about the implantable lead.

13. The method of claim 12, wherein removeably securing the proximal end of the implantable lead within the lumen of the insertion tool comprises sliding the insertion tool from the proximal end until the lumen of the insertion tool frictionally engages the implantable lead.

14. The method of claim 12, wherein applying the longitudinal force, along the length of the implantable lead, to the insertion tool comprises frictionally engaging the insertion tool with the implantable lead.

15. The method of claim 12, wherein removing the insertion tool comprises applying the splitting force in a direction opposite the implantable medical device.

* * * * *